(12) United States Patent
Takeda et al.

(10) Patent No.: US 9,341,550 B2
(45) Date of Patent: May 17, 2016

(54) METHOD FOR DETECTING LOW CONCENTRATIONS OF SPECIFIC CELL FROM HIGH CONCENTRATIONS OF CELL POPULATIONS, AND METHOD FOR COLLECTING AND ANALYZING DETECTED CELL

(75) Inventors: Kazuo Takeda, Tokyo (JP); Fumie Jimma, Tokyo (JP); Masashi Takao, Miyagi (JP)

(73) Assignee: ON-CHIP BIOTECHNOLOGIES CO., LTD., Tokyo (JP)

( * ) Notice: Subject to any disclaimer, the term of this patent is extended or adjusted under 35 U.S.C. 154(b) by 210 days.

(21) Appl. No.: 13/885,570

(22) PCT Filed: Nov. 21, 2011

(86) PCT No.: PCT/JP2011/076800
§ 371 (c)(1),
(2), (4) Date: Jul. 30, 2013

(87) PCT Pub. No.: WO2012/067259
PCT Pub. Date: May 24, 2012

(65) Prior Publication Data
US 2013/0302828 A1 Nov. 14, 2013

(30) Foreign Application Priority Data
Nov. 19, 2010 (JP) .................................. 2010-258934

(51) Int. Cl.
| | | |
|---|---|---|
| G01N 33/543 | (2006.01) | |
| G01N 33/566 | (2006.01) | |
| G01N 33/577 | (2006.01) | |
| G01N 35/08 | (2006.01) | |
| G01N 33/574 | (2006.01) | |
| G01N 1/30 | (2006.01) | |
| G01N 15/14 | (2006.01) | |
| G01N 15/10 | (2006.01) | |

(52) U.S. Cl.
CPC .............. *G01N 1/30* (2013.01); *G01N 15/1459* (2013.01); *G01N 33/54333* (2013.01); *G01N 33/574* (2013.01); *G01N 2015/1006* (2013.01); *G01N 2015/1477* (2013.01); *G01N 2333/70596* (2013.01)

(58) Field of Classification Search
None
See application file for complete search history.

(56) References Cited

U.S. PATENT DOCUMENTS

| | | |
|---|---|---|
| 2002/0172987 A1 | 11/2002 | Terstappen et al. |
| 2004/0018621 A1* | 1/2004 | Reid et al. ..................... 435/370 |
| 2007/0026469 A1 | 2/2007 | Fuchs et al. |
| 2008/0069300 A1 | 3/2008 | Saito |
| 2011/0294139 A1 | 12/2011 | Takeda |

FOREIGN PATENT DOCUMENTS

| | | | |
|---|---|---|---|
| JP | 2006-029921 A | | 2/2006 |
| JP | 2007-178193 A | | 7/2007 |
| JP | 2010-181349 A | | 8/2010 |
| WO | WO2011/057034 | * | 5/2011 |

OTHER PUBLICATIONS

Takao M. et al., Expanded Applications of New-Designed Microfluidic Flow Cytometer (Fishman-R), Cytometry Part B, (2009), CCS Abstracts, p. 405, 30.
Takeda K., et al., Maintenance Free Biosafety Flow Cytometer Using Disposable Microfluidic Chip (Fishman-R), Cytometry Part B, (2009), CCS Abstracts, p. 405-406, 31.
BioJapan2010 World Business Forum, (Sep. 2010), http://exponet.nikkeipb.co.jp/bio2010/exhibitor/ja/company/exhibitor_269.html, [retrieval date Feb. 2, 2012].
Wlodkowic D., et al., Cytometry in Cell Necrobiology Revisited. Recent Advances and New Vistas, Cytometry Part A, (published online Mar. 2010), vol. 77A, No. 7, p. 591-606.
Satoshui Matsuzaka, "Kotai Iyaku ni Taisuru Biomarker", Journal of Clinical and Experimental Medicine, (2009), vol. 228, No. 11, pp. 1105 to 1108.
Masashi Takao et al., "Flow cytometric detection of circulating tumor cells (CTC): Intact CTC enumeration and analysis", Cytometry Res. (Mar. 2011), vol. 21, No. 1, pp. 51 to 56.
Takao M. et al., Enumeration, Characterization and Collection of Intact Circulating Tumor Cells by Cross Contamination-Free Flow Cytometry, Cytometry Part A, (Feb. 2011), vol. 79A, No. 2, p. 107-117.
Tom Kojima et al., "A simple biological imaging system for detecting viable human circulating tumor cells", The Journal of Clinical Investigation, Oct. 2009, vol. 119, No. 10, pp. 3172-3181.
Masashi Takao et al., "Enumeration and Characterization of Circulating Tumor Cells With Cross-Contamination Free Flow Cytometer", ISAC 2010 Program and Abstract, 2010, p. 180.

* cited by examiner

*Primary Examiner* — Karen Canella
(74) *Attorney, Agent, or Firm* — Heslin Rothenberg Farley & Mesiti P.C.

(57) ABSTRACT

Conventional CTC detection methods have been problematic in that 1) there is no technique for automatically determining and counting live CTCs in a brief period of time, 2) no process has been developed for detecting, counting, and thereafter collecting and culturing live CTCs, and 3) there exists no flow cytometer that is contamination free and is capable of measuring an entire sample. Provided is a CTC detection method which comprises a pre-treatment step for concentrating and fluorescence staining CTCs, and a step for identifying and counting CTCs. The pre-treatment step includes attaching magnetic beads to EpCAM antibodies expressed by epithelial cell-derived CTCs and concentrating the CTCs through the use of a magnet, fluorescently labeling an epithelia cell surface marker of the CTCs through the use of EpCAM antibodies or 5E11 antibodies, and performing two types of nuclear staining, one being cell membrane-permeable and the other being cell membrane-impermeable. The identifying and counting step includes evaluating the respective absolute concentrations of live and dead CTCs in a volume of blood by automatically identifying CTCs by the ratio of a plurality of fluorescence signal intensities using a flow cytometer, and differentiating between and counting the live CTCs and the dead CTCs. In the cytometer, an entire liquid-feeding system that includes a flow cell can be replaced for each sample, and the total amount of a liquid sample can be measured.

7 Claims, 10 Drawing Sheets

20: CD326 antibody immobilized magnetic beads

21: APC fluorescence labeled CD326 antibody

22: APC fluorescence labeled 5E11 antibody

23: APC antibody immobilized magnetic beads

Method for identifying cells stained with APC in FL3 vs FL4 scatter diagram
FL3/FL4 = constant
Log FL3 = Log FL4 + Log constant
(Formula shows cell distribution on the straight line in the above scatter diagram)

Fig. 8A
Procedure of automatic live CTC identification

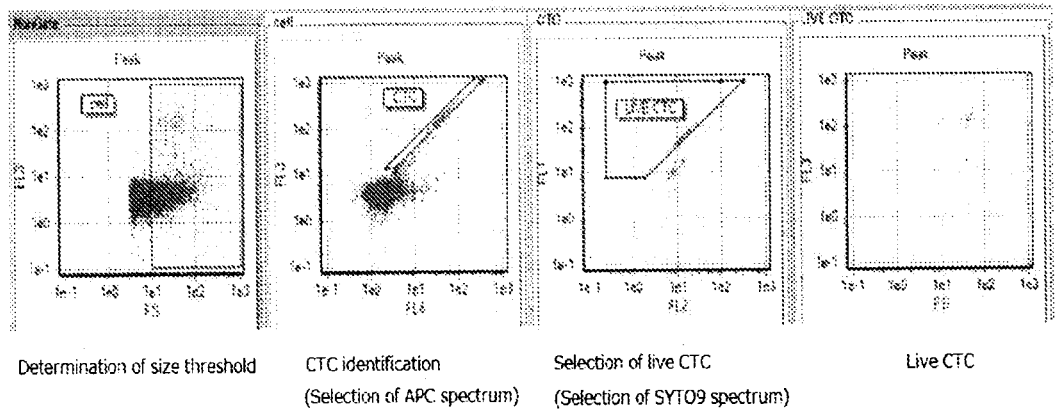

Determination of size threshold    CTC identification    Selection of live CTC      Live CTC
                                (Selection of APC spectrum)    (Selection of SYTO9 spectrum)

Fig. 8B
Procedure of automatic dead CTC identification

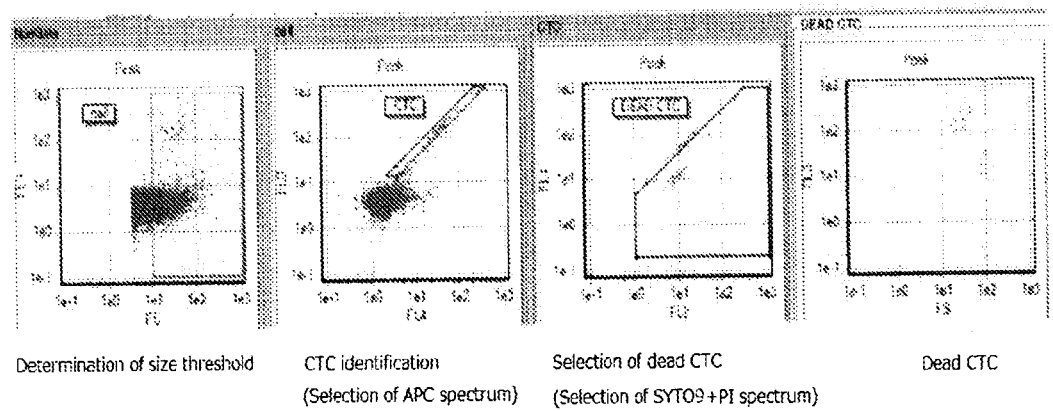

Determination of size threshold    CTC identification    Selection of dead CTC      Dead CTC
                                (Selection of APC spectrum)    (Selection of SYTO9+PI spectrum)

Fig. 8C
Importance of removal of non-specific APC stained cells in CTC identification

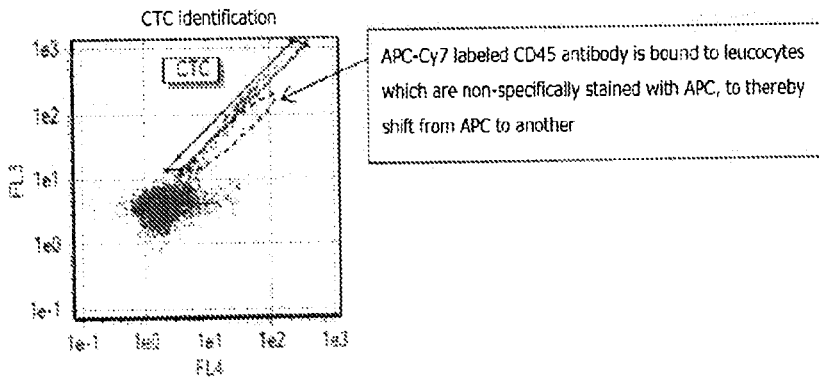

METHOD FOR DETECTING LOW CONCENTRATIONS OF SPECIFIC CELL FROM HIGH CONCENTRATIONS OF CELL POPULATIONS, AND METHOD FOR COLLECTING AND ANALYZING DETECTED CELL

TECHNICAL FIELD

The present invention relates to a method for detecting specific cells from high concentrations of cell populations, such as a method for detecting circulating tumor cells, and a method for treating cancer using the same.

BACKGROUND ART

Recently, it has been reported that a circulating tumor cell (CTC), circulating endothelial cell (CEC) or bone marrow derived-circulating endothelial progenitor (CEP) is useful as a biomarker for estimating an effect of chemotherapy (NON-PATENT LITERATURE 1). The detection of the circulating tumor cell (CTC) has the following advantageous effects. That is to say, it is useful for detecting a metastatic cancer or treating cancer to detect the circulating cancer cells in blood, for the following reasons.
(1) A cancer metastasis means that cancer cells detached from cancer tissues migrate to peripheral blood and proliferate in other tissues reached.
(2) It is reported that the number of CTCs correlates with cancer metastasis and prognosis.
(3) Clinically, a degree of progression, degree of malignancy, and prognosis of breast cancer are diagnosed by the number of CTCs.

When such cancer cells are detected in peripheral blood of a cancer patient, it is necessary to detect very low concentrated cells which are approximately one billionth of the high concentrated blood cells. Therefore, a count loss of cancer cells or a cross-contamination between samples of patients leads to a serious misdiagnosis. As an example of the measurement of CTCs, a Cell Search System (U.S.A), which is only a commercially-available product, is used. A method used in the Cell Search System is disclosed in PATENT LITERATURE 1 and NON-PATENT LITERATURE 1. In particular, cells are subjected to nuclear staining and cytokeratin staining, and react with CD326 antibody immobilized-magnetic beads. The cells are surfaced by a magnetic field, and scanned with a laser beam to obtain fluorescent imaging of the cell. Then, someone decides whether or not the cell is CTC from the fluorescent imaging, and thus the judgment is not an automatic one by an apparatus. Further, there is a method called CTC-chip. The method is disclosed in PATENT LITERATURE 2. In particular, a chip, wherein 80,000 micro posts are formed on a silicon wafer the size of a business card, is used. These 80,000 micro posts are immobilized with an anti-CD326 antibody. Blood is applied to the chip, and then the number of CTCs is measured by recognizing all images of the micro posts. PATENT LITERATURE 3 discloses the following method. Specifically, the CTCs detected by the method disclosed in PATENT LITERATURE 1 are collected, and then the CTCs are genetically analyzed by a fluorescence in situ hybridization (FISH). Further, NON-PATENT LITERATURE 2 discloses a method using a virus with which cancer cells can be specifically infected. The cancer cells are infected with the virus to thereby express a fluorescence protein i.e. the GFP and the cancer cells are detected by a fluorescence microscope. Even further, NON-PATENT LITERATURE 4 describes a method for isolating specific cells from cell population containing many types of cells. In particular, antigen-antibody reactions are carried out by bringing multiple types of thermoresponsive magnetic particles which are immobilized with different types of antibodies respectively, into contact with many types of cell populations. Then, based on the antigen-antibody reactions, many types of cell populations are selectively separated by serially carrying out separations using a gradient field at various temperatures. The numbers of the separated cells are measured by a flow cytometer having a flow cell capable of collecting a sample liquid, and then the cells are collected.

In addition, as a basic research reagent kit for magnetically concentrating CTCs in peripheral blood, the CD326 (Ep-CAM) Tumor Cell Enrichment and Detection Kit (Miltenyi Biotec, Catalog #130-090-500) is known. This kit is composed of magnetic beads immobilized with CD326(EpCAM) antibody, a fluorescence labeled anti-cytokeratin antibody, and the like. In the kit, the fluorescence of cytokeratin staining must be detected. Therefore, all the concentrated cells are dead by staining intracellular cytokeratin. Further, a reagent kit for magnetically concentrating epithelial cells, i.e. the HUMAN EpCAM POSITIVE SELECTION KIT (Stem Cell Technologies, Catalog #18356) is also known. However, a protocol for concentrating CTCs in blood is not described in its catalog. Further, a reagent kit (Tumor Cell Enrichment Cocktail (Stem Cell Technologies, Catalog #15167)) for negatively selecting CTCs in blood is also known. In the reagent kit, erythrocytes and leucocytes, which are not intended cells, are cross-linked using antibodies and are subjected to a density gradient centrifugation thereof. However, there is no demonstrable indication that the cells concentrated by the reagent kit are only CTCs. Further, a reagent kit (Tumor Cell Enrichment Cocktail (Stem Cell Technologies, Catalog #14152)) for concentrating CTCs by negative selection using antibody-immobilized magnetic beads and a magnet, is also known. However, there is no demonstrable indication that the cells concentrated by the reagent kit are only CTCs. In magnetic beads immobilized with an antibody against a fluorescence molecule, i.e. allophycocyanin (hereinafter referred to as "APC") (APC Selection Kit (Stem Cell Technologies, Catalog #18451)), APC is labeled with an antibody, and then a magnetic bead is bound to APC. Further, PATENT LITERATURE 5 discloses a technology of a conventional flow cytometer in which a liquid-feeding system containing a flow cell is fixed.

CITATION LIST

Patent Literature

[PATENT LITERATURE 1] US20020172987
[PATENT LITERATURE 2] US20070026469
[PATENT LITERATURE 3] Japanese Unexamined Patent Publication (Kokai) No. 2007-178193
[PATENT LITERATURE 4] Japanese Unexamined Patent Publication (Kokai) No. 2010-181349
[PATENT LITERATURE 5] Japanese Unexamined Patent Publication (Kokai) No. 2006-29921

Non-Patent Literature

[NON-PATENT LITERATURE 1] IGAKUNO AYUMI, Vol. 228, No. 11, 2009, p. 1105-1108
[NON-PATENT LITERATURE 2] The Journal of Clinical Investigation Volume 119 Number 10 Oct. 2009

[NON-PATENT LITERATURE 3] ISAC2010 Program and Abstract, 2010, p. 180

SUMMARY OF INVENTION

Technical Problem

In a method for detecting and measuring the CTCs, low numbers of specific cells (about 1 cell/mL) are detected from and counted in high concentrations of cell populations (about $10^9$ cells/mL). However, a method wherein cross-contamination between samples is free (CTCs are concentrated alive, the living CTCs are distinguished from dead CTCs and measured, and further, the CTCs can be collected alive) has not been reported until now.

For example, regarding the method disclosed in PATENT LITERATURE 1 as the method for detecting CTCs, an apparatus, called a "Cell Search System", for carrying out the method is a commercial reality. In the method disclosed in PATENT LITERATURE 1, images of any candidate cells are obtained by the apparatus. Then, a decider determines whether or not a candidate cell is a cell of interest, according to the decider's image recognition. The disadvantage of the method is as follows. The decision can not be carried out automatically. Further, in order to detect the CTC, it is necessary to stain cytokeratin in cell by a fluorescence-labeled antibody. That is to say, a cell membrane of the CTC is perforated by the cytokeratin staining and, thus, the CTC is dead. Therefore, the stained cells can not be cultured.

In the method disclosed in PATENT LITERATURE 2, the specific cells are trapped using an antibody on approximately 80,000 micro posts formed in the chip, and the trapped cells are measured via image recognition. However, there is a problem in that it takes 8 hours or more to recognize all 80,000 micro post images.

In the method disclosed in NON-PATENT LITERATURE 2, the CTCs in peripheral blood collected from a patient are infected with the virus with which cancer cells may be specifically infected. Then, CTCs wherein the GFP of the virus are expressed are detected by a fluorescence microscope. It takes one day or more to detect GFP expressed sufficiently. Thus, the detection of GFP is 2 days after blood collection at the earliest. Further, due to the viral infection, the cells cannot be cultured.

As shown in PATENT LITERATURE 5, in the conventional flow cytometer in which the liquid-feeding system containing a flow cell is fixed, preclusion of the possibility of the cross-contamination between samples is impossible. Further, in the liquid-feeding system, a sample liquid in a sample tube is taken up by a capillary, and then the sample liquid is allowed to flow into the flow cell. Therefore, a part of the sample liquid remains in the bottom of the sample tube, and thus, in principle, it is impossible to measure the whole sample liquid. That is to say, in the conventional flow cytometer in which the whole sample liquid can not be measured, the total number of cells in the sample can not be evaluated. Furthermore, the cells are settled out by gravity and thus the cells are concentrated in the bottom of the sample liquid as time advances. However, measuring the whole sample liquid in order to absolutely evaluate the cell concentration is necessary.

PATENT LITERATURE 4 discloses the technology of the flow cytometer of contamination-free but does not disclose a method for measuring the whole sample liquid using the same.

Further, NON-PATENT LITERATURE 3 discloses a method wherein the CTCs are concentrated by magnetic beads and measured while distinguishing living cells from dead cells. However, when CTCs were experimentally added to a sample, a CTC detection efficiency is only 70%. Furthermore, NON-PATENT LITERATURE 3 does not disclose the method for measuring the whole sample liquid.

The problems of the above conventional methods are classified into the following.

First Problem

There is no technique for automatically determining and counting live CTCs in a brief period of time.

Second Problem

No process has been developed for detecting, counting, and thereafter collecting and culturing live CTCs. In the process, it is necessary to preclude the cross-contamination between samples for cell culture, and aseptically treat cells for culture.

Third Problem

In the conventional flow cytometers wherein CTCs are automatically measured in a short period of time, there exists no flow cytometer that is both contamination free and capable of measuring an entire sample. Further, another conventional measurement method can not solve the first problem.

The present invention provides a method capable of solving the above three problems simultaneously.

Solution to Problem

The present inventors have conducted intensive studies into a method for counting a small amount of cells contained in a large amount of cells by measuring an entire sample without cross-contamination, and as a result, found that the above problems can be solved by measuring the whole sample liquid using a flow cytometer having a disposable micro flow-path chip as a flow cell, containing a sample reservoir, a collection reservoir, and a micro flow-path from the bottom of the sample reservoir to the bottom of the collection reservoir on a substrate. In particular, the inventors found that, according to the micro flow-path chip, the whole sample liquid can flow directly into the micro flow path from the bottom of the sample reservoir, and the end point of the whole sample liquid can be detected by air bubbles generated after finishing a flow of the whole sample liquid The present invention is based on the above findings.

Namely, the present invention relates to:

[1] a method for enumeration of specific cells present in highly dense cells, characterized by comprising:
the pretreatment step of concentrating the specific cells, and fluorescence staining said cells, and
the step of counting all the specific cells in the sample liquid by automatically identifying said cells based on fluorescence signal intensity thereof;
wherein, in the counting step, the specific cells are counted by measuring a whole sample liquid by a flow cytometer having a disposable micro flow-path chip as a flow cell, the micro flow-path chip containing a sample reservoir, a collection reservoir, and a micro flow-path connected from the bottom of the sample reservoir to the bottom of the collection reservoir on a substrate; and an end point of the whole sample liquid is recognized by a detection of air bubbles generated in the micro flow-path just when the sample liquid in the sample reservoir flows out,

[2] the method for enumeration of the specific cells of item [1], wherein the specific cells are concentrated alive in the pretreatment step and the numbers of living cells and dead cells of the specific cells are separately counted in the counting step,

[3] a method for enumeration of circulating tumor cells (CTCs) by detecting the CTCs present in peripheral blood containing highly dense blood cells, characterized by comprising:

the pretreatment step including a treatment for concentrating the CTCs and a treatment for fluorescence staining the CTCs, and the step of identifying and counting the CTCs;

wherein, the pretreatment step comprises a treatment for concentrating CTCs by binding magnetic beads to EpCAM, which is expressed on CTCs derived from epithelial cells using a magnet, and a treatment for fluorescence staining the CTCs with anti-EpCAM antibody or 5E11 antibody; and in the CTC identifying and counting step, CTCs are counted by measuring a whole sample liquid using a flow cytometer having a disposable micro flow-path chip as a flow cell, which contains a sample reservoir, a collection reservoir, and a micro flow-path connected from the bottom of the sample reservoir to the bottom of the collection reservoir on a substrate, and an end point of the whole sample liquid is recognized by a detection of air bubbles generated in the micro flow-path just when the sample liquid in the sample reservoir flows out,

[4] the method for enumeration of circulating tumor cells (CTCs) of item [3], wherein the pretreatment step further comprises treatments of two types of nuclear staining, one being cell membrane permeable nuclear staining and the other being cell membrane non-permeable nuclear staining; and in the identifying and counting step, the number of the CTCs are measured separately, divided into living CTCs and dead CTCs,

[5] the method for enumeration of circulating tumor cells (CTCs) of item [4], wherein the pretreatment step comprises a treatment for concentrating CTCs by binding anti-EpCAM antibody-immobilized magnetic beads to CTCs using a magnet, a treatment for fluorescence staining the CTCs with an APC labeled anti-EpCAM antibody, and a treatment for nuclear staining of the CTCs with SYTO9 and PI; and in the identifying and counting step, the CTC is recognized by identifying the APC fluorescence spectrum using a ratio between two types of fluorescence signal intensities generated by light excitation at a wavelength of around 640 nm, and life or death of CTCs is determined by the fluorescence signals of SYTO9 and PI, which are generated by light excitation at a wavelength of around 480 nm, in the identifying and counting step,

[6] the method for enumeration of circulating tumor cells (CTCs) of item [5], wherein a APC labeled 5E11 antibody is used instead to the APC labeled anti-EpCAM antibody, in the pretreatment step,

[7] the method for enumeration of circulating tumor cells (CTCs) according to claim 3, wherein the treatment for concentrating CTCs comprises fluorescent staining by the APC labeled anti-EpCAM antibody, and binding anti-EpCAM antibody-immobilized magnetic beads to CTCs,

[8] the method for enumeration of circulating tumor cells (CTCs) of item [5], wherein a blue laser power for PI fluorescence excitation is one-tenth (1/10) or less of a red laser power for APC fluorescence excitation in order to analyze the recognition of CTC by an APC fluorescence signal and the recognition of death cells by PI simultaneously, or

[9] a method for simultaneously counting the number of at least two types of cells selected from the group consisting of CTC, CEC, and CEP, comprising steps of:

removing leucocytes by negative selection using magnetic beads immobilized with an antibody, against an antigen which is expressed on leucocytes but not expressed on CEC and/or CEP, and fluorescence staining cells, which do not bind to the antibody immobilized-magnetic beads, with at least two antibodies selected from the group consisting of anti-CD326 antibody for detecting CTC, anti-CD146 antibody for detecting CEC, and anti-CD133 antibody for detecting CEP, respectively.

Further, the present specification discloses:

[1] a method for enumeration of specific cells present in highly dense cell populations, characterized by comprising:

the pretreatment step of magnetically-concentrating the specific cells and fluorescence staining the specific cells, and the step of measuring the specific cells by automatically recognizing the specific cells based on a fluorescence signal intensity thereof; wherein, in the measurement step, the specific cells are recognized by a flow cytometer capable of measuring the total cell numbers in a whole sample liquid, in which the entire liquid-feeding system containing a flow cell is replaceable with respect to each sample, and living cells and dead cells separately counted,

[2] the method for enumeration of the specific cells of item [1], wherein the flow cytometer having a disposable microfluidic chip as the flow cell is used in the cell detection process, and the measurement of the whole sample liquid is confirmed by detecting signals of air bubbles generated in the micro flow-path just when the sample liquid flows out from the bottom of a sample reservoir formed on a micro flow-path chip substrate, as an end point signal,

[3] a method for evaluating CTC concentration by detecting low-concentrated circulating tumor cells (CTCs) from peripheral blood containing high density blood cell populations, comprising:

the pretreatment step comprising a concentration of the CTCs and a fluorescence stain of the CTCs, and the step of identifying and measuring the CTCs;

wherein, the pretreatment step comprises a treatment for concentrating CTCs by binding magnetic beads to EpCAM which is expressed on CTCs derived from an epithelial cell using a magnet, a treatment for fluorescence staining a epithelial cell's surface marker expressed on CTC with anti-EpCAM antibody or 5E11 antibody, and a treatment of two types: cell membrane permeable nuclear staining and cell membrane non-permeable nuclear staining; and in the CTC-identifying and measuring step, respective absolute concentrations of live or dead CTCs in a blood volume are evaluated by automatically identifying CTCs by a ratio of plural fluorescence intensities, and separately measuring living cells and dead cells, using a flow cytometer in which the entire liquid-feeding system containing a flow cell is replaceable with respect to each sample, and the whole ample liquid can be measured thereby,

[4] the method for evaluating CTC concentration of item [3], wherein the flow cytometer used in the CTC-identifying and measuring step has a disposable micro flow-path chip as a flow cell, and the whole sample liquid is measured by detecting signals of air bubbles generated in the micro flow-path connected to the bottom of a sample reservoir formed on a micro flow-path chip substrate just when the sample liquid flows out, as an end point signal,

[5] the method for evaluating CTC concentration of item [3], wherein the pretreatment step comprises a reaction for binding anti-human EpCAM antibody-immobilized magnetic beads to CTCs, a treatment for fluorescence staining the CTCs with a APC labeled anti-human EpCAM antibody, and a treatment for nuclear staining of the CTCs with SYTO9 and PI; and in the CTC-identifying and measuring step, CTC is identified by recognizing the APC fluorescence spectrum using a ratio between two types of fluorescence signal intensities generated by light excitation at a wavelength of around 640 nm, and the determination of life or death of CTCs is carried out by the fluorescence signals of SYTO9 and PI which are generated by light excitation at a wavelength of around 480 nm,

[6] the method for evaluating CTC concentration of item [3], wherein the treatment for concentrating CTCs comprises a reaction of the anti-human EpCAM antibody-immobilized magnetic beads and fluorescence labeled human 5E11 antibody,

[7] the method for evaluating CTC concentration of item [3], wherein the treatment for concentrating CTCs comprises a process of antibody reaction of an APC labeled anti-human EpCAM antibody and magnetic beads immobilized with antibody against APC,

[8] the method for counting CTCs of item [3], wherein the CTC-identifying and measuring step comprises a process of recognizing CTCs and a process for determining life or death of CTCs,

[9] the method for evaluating the number of CTCs of item [3], wherein the treatment for fluorescence staining CTCs comprises a nuclear staining of death cells by PI, and a staining of CTCs by APC labeled EpCAM antibody; and a blue laser power for PI fluorescence excitation is one-tenth ($1/10$) or less of a red laser power for APC fluorescence excitation in order to analyze the recognition of CTC by APC fluorescence signal and the recognition of death cells by PI simultaneously,

[10] a method for simultaneously counting concentrations of plural biomarkers, i.e. a method for simultaneously detecting and counting CTCs and CECs or CEPs, which is another biomarker, comprising steps of: lysing erythrocytes, removing leucocytes by negative selection using magnetic beads immobilized with an antibody against an antigen which is not expressed on CEC and/or CEP, among surface markers expressed on leucocytes, and fluorescence staining cells which do not bind to the antibody immobilized-magnetic beads, with anti-CD326 antibody for detecting CTC, anti-CD146 antibody for detecting CEC, and anti-CD133 antibody for detecting CEP, respectively.

Under these circumstances, the following method for evaluating specific cells is provided in the present invention.

The method for enumeration of specific cells is evaluating the number of a few specific cells present in highly dense cells. The method is characterized by comprising a pretreatment step of carrying out a treatment for concentrating the specific cells from the large number of concentrated cells by binding antibody-immobilized beads to the specific cells and using a magnetic field, and a treatment for fluorescence staining the specific cells for detection; and a step for counting the specific cells based on a fluorescence signal intensity thereof. The step for counting the specific cells is characterized by a flow cytometer wherein an entire liquid-feeding system containing a flow cell is replaceable with respect to each sample and the total cell number in a whole sample liquid can be measured.

In the step for counting specific cells in the method for enumeration of specific cells of the present invention, the specific cells may be counted with the determination of life or death of CTCs, or may be counted without the determination of life or death of CTCs. The specific cells are not particularly limited, so long as the specific cells are a few cells included in the large numbers of cells. For example, there may be mentioned a circulating tumor cell (CTC), a circulating endothelial cell (CEC) or a bone marrow-derived circulating endothelial progenitor (CEP). In addition, the number of "a few cells" as used herein is not limited, so long as a concentration of cells is $1/10^5$ cells or less with respect to blood cells in the body, preferably $1/10^6$ or less, more preferably $1/10^7$ or less, even more preferably $1/10^8$ or less, most preferably $1/10^9$ or less. For example, it is known that a concentration of CTC detected from a cancer patient in an early stage is typically about 1 cell/mL, and thus it is estimated that the total number of CTC contained in 5 mL of blood is approximately 5 cells. In order to accurately measure such a low dense cells, it is effective to measure a whole sample liquid. In a conventional flow cytometer, a part of the whole sample liquid is measured, and the total numbers of cells contained in the whole sample liquid is calculated from the obtained cell number thereof. In order to accurately calculate the total number of cells in the above method, it is necessary that the concentration of cells in the sample liquid is even. However, the cells in the sample liquid settle out under the influence of gravity, and thus, the concentration of cells therein is not even. Therefore, in the absolute measurement of specific cells contained in the sample liquid, remarkable effects of the present invention are obtainable.

In the method of the present invention, the detection process is characteristic, as follows.

In the flow cytometer used in the above process for detecting cells, the disposable micro flow-path chip shown in FIG. 1 is used as a flow cell. As shown in FIG. 2, the flow cytometer has a laser light source, a forward-scattered light detector 62, a side-scattered light detector 67, and multiple fluorescence detectors 63, 64, 65, 66. In the method for measuring the whole sample liquid by using the flow cytometer, the whole sample liquid may flow out to a micro flow path by applying air pressure to a sample reservoir 1 formed on the micro flow-path chip substrate. Therefore, the sample liquid may be measured until all of the sample liquid flows out. As shown in FIG. 3(a), the air bubbles are generated in the flow path just after all of the sample liquid flows out. Therefore, the measurement is automatically finished with the detection of air bubble signals as an end point of the sample liquid. After the measurement, the numbers of cells are evaluated only from the data from the signal detections without the air bubble signals, and the cell concentration is evaluated completely by all cell numbers contained in the entire volume of the measured sample liquid.

As the micro flow-path chip (flow cell), the "flow cell comprising: a first flow path in which a sample liquid containing particles is introduced, a second flow path and a third flow path arranged on both sides of the first flow path and a fourth flow path joining the first, second, and third flow paths, which are formed on a substrate; wherein the flow cell has the first to third flow paths on the upstream side, and fifth to seventh flow paths on the downstream side, further has a first reservoir on the downstream side of the first to third flow paths, and a second reservoir on the upstream side of the fifth to seventh flow paths flow path respectively, the second and third flow paths for introduction of a sheath liquid are connected to the first reservoir, the first flow path for introduction of a sample liquid is connected to a third reservoir that is formed within the first reservoir, a sheath liquid level of the second and third flow paths is common in the first reservoir, the third reservoir is independent from the first reservoir so as not to mix the sheath liquid and sample liquid in the first reservoir, the middle fifth flow path on the downstream side is connected to a fourth reservoir that is formed within the second reservoir, the sixth and seventh separation flow paths on both sides thereof are connected to the second reservoir, an atmospheric gas with constant pressure higher than the atmospheric pressure is introduced to the first reservoir using a removable cap structure, a flow rate of the sample liquid is constantly controlled by the atmospheric gas pressure in an apparatus for measuring a particle in a solution, the first to third flow paths on the upstream side and the fifth to seventh flow paths on the downstream side are symmetrically arranged, the sample liquid is collected into the fourth reservoir on the downstream side, and the sheath liquid is collected into the second reservoir" disclosed in Japanese Patent 4358888 can be used.

The method for evaluating the concentration of CTCs will be described hereinafter.

The method for evaluating a concentration of CTCs is characterized by the following steps in the method for detecting a low-dense, circulating tumor cells (CTCs) from peripheral blood containing highly dense blood cell populations. The method is comprised of a pretreatment step with a concentration of live CTCs and a fluorescence stain of CTCs, and the step of identifying and counting the CTCs. The pretreatment step comprises, for example, a treatment for specifically concentrating CTCs by binding magnetic beads immobilized with an antibody against a surface marker expressed on CTCs derived from human epithelial cells to CTCs and using a magnet, a treatment for fluorescent staining via an antibody against the surface marker expressed on CTCs derived from human epithelial cell, and a treatment of two types of permeable cell membrane nuclear staining and non-permeable cell membrane nuclear staining. In the CTC-identifying and counting step, respective absolute concentrations of live or dead CTCs in a blood volume are evaluated by automatically identifying CTCs by ratio of multiple fluorescence intensities, and separately measuring living cells and dead cells, using a flow cytometer in which the entire liquid-feeding system containing a flow cell is replaceable with respect to each sample, and the whole sample liquid can be measured thereby.

In the present invention, the treatment of two types of permeable cell membrane nuclear staining and non-permeable cell membrane nuclear staining, and the procedure for separately measuring living cells and dead cells are optional steps. Therefore, it is preferable to carry out these steps, but the present invention includes the method for evaluating a concentration of CTCs without these steps. Further, CTC is not limited to one derived from human, but includes ones derived from mammal such as canine, feline, bovine, horse, rabbit, mouse, or rat.

In the above method, it is preferable to concentrate and stain the CTCs alive, and separately measure living CTCs and dead CTCs by measuring total volume of the sample so as to evaluate the concentration thereof, respectively. In particular, the method is carried out as follows.

In the treatment for concentrating CTCs and staining CTCs alive in the above method, the cytokeratin staining wherein a cell membrane is perforated, is not carried out, and CTCs are specifically concentrated and fluorescently stained by magnetically concentrating and staining using the antibody against the surface marker of the CTC derived from epithelial cells. In the flow cytometer used in the CTC-identifying and counting step, the disposable micro flow-path chip shown is used as the flow cell. The total volume of the sample is measured by detecting signals of air bubbles generated in the micro flow-path connected to the bottom of a sample reservoir formed on a micro flow-path chip substrate just after the sample liquid flows out, as an end point signal, and whereby a count loss of CTCs can be extremely reduced in the method for evaluating a concentration of CTCs of the present invention.

In the above method, for example, the following antibodies and fluorescent labels can be used as the antibodies and fluorescent labels for concentrating and staining CTCs The magnetic beads immobilized with an anti-human EpCAM antibody are used as the magnetic beads for magnetically concentrating CTCs. Either the APC labeled anti-human EpCAM antibody or the APC labeled anti-human 5E11 antibody is used as a specific antibody for fluorescence staining CTCs. Further, SYTO9 and PI are used as nuclear staining agents for determining whether the CTC is alive or dead. This embodiment using the specific antibody for fluorescence staining CTCs corresponds to Type A and Type B in the "antibody reaction" of the process flow chart shown in FIG. 4. In the case of Type A, the specific antibody for fluorescence staining CTCs binds to the surface marker to which the antibody used in the magnetic beads binds. Therefore, that may possibly cause the competitive inhibition. However, there is no practical problem in accordance with the actual obtained data. In the case of Type B, there is no problem on the competitive inhibition. As shown in FIG. 2, in the CTC identifying and counting step, an apparatus having an optical detection system which can illuminate the cells with two types of lasers (a blue laser with emission wavelength range from 470 to 490 nm, and a red laser with emission wavelength range from 630 to 650 nm) simultaneously, and detect 4 or more fluorescence signals, is used, and CTCs are identified and analyzed as follows. That is to say, fluorescence is developed by red laser illumination, and two fluorescence signals at different wavelengths are detected as shown in FIG. 6(a). Further, as shown in FIG. 6(b), the APC fluorescence spectrum is recognized by a rate of the two signal intensities. The detected cells with the same rate are found on a straight line as shown in FIG. 6(b). If a detected fluorescence spectrum is different from that of the APC, a rate of two signal intensities thereof is also different from that of the APC. Thus, cells with the fluorescence spectrum other than that of the APC are found on a different straight line, and the cells with the other fluorescence spectrum can be distinguished from the cells with the APC. In this manner, the cells with fluorescence spectrum of the APC are automatically recognized as the CTCs. As cells other than CTCs stained by the APC, leucocytes are sometimes non-specifically stained thereby. Therefore, the leucocytes are distinguished from the CTCs by staining the leucocytes with APC-Cy7 labeled anti-CD45 antibody and shifting from the APC fluorescence spectrum to an APC-Cy7 fluorescence spectrum. Further, life or death of CTCs is determined by fluorescence signals of SYTO9 and PI developed by blue laser illumination. That is, a CTC stained only with SYTO9 is determined as a live CTC, and a CTC stained both with SYTO9 and PI is determined as a dead cell. However, there is a problem in the fluorescence spectrum recognition of APC and the fluorescence spectrum recognition of SYTO9 and PI, as will be noted from the fluorescence spectrum shown in FIG. 7(a). That is to say, the fluorescence spectrum of PI excited by a blue laser, and the fluorescence spectrum of APC excited by a red laser are overlapped. Thus, the detection signal of APC fluorescence and the detection signal of PI fluorescence are mutually interfered.

In order to solve the aforementioned problem, the blue laser's power is set to one-tenth (1/10) or less of the red laser's power so that the PI fluorescence signal at FL3 and FL4, which are signals for APC detection, is reduced to an ignorable level. That is, as shown in FIG. 7(b), the detection signal of APC fluorescence and the detection signal of PI fluorescence can be independently analyzed by setting the laser power at 473 nm to 1 mW or less and the laser power at 640 nm to 30 mW or more. And whereby it has become possible that an identification of CTC by recognizing the APC spectrum and a determination of life or death of the CTC are carried out simultaneously. One of the advantages of this analyzing method is that the fluorescence correction which is essential in a conventional flow cytometry, is unnecessary.

Further, in the above method, the treatment for concentrating CTCs can comprise the process of antibody reaction of the APC labeled anti-human EpCAM antibody to CTCs and the process of antibody reaction of magnetic beads immobilized with antibodies against the APC to CTCs. This embodiment corresponds to Type C in the "antibody reaction" of the process flow chart shown in FIG. 4. In this case, the concentration of cells is dependent on the specificity of one type of antibody, i.e. the CD326 antibody. Therefore, there is no problem on the competitive inhibition.

Further, a method for accurately evaluating a cancer progression by simultaneously detecting other biomarker(s) such as CEC and/or CEP in addition to CTC, will be illustrated hereinafter. In the present invention, two biomarkers selected from a group consisting of CTC, CEC, and CEP, may be detected simultaneously, and the three biomarkers may be detected simultaneously.

In the treatment for concentrating the CEC and/or the CEP which are detected along with the CTC, the CEC and/or CEP are not positively selected by using magnetic beads immobilized with an antibody against the respective surface marker, but negatively selected by using magnetic beads immobilized with an antibody against cells other than the CEC and the CEP, in the magnetic concentration. That is, erythrocytes are removed by hemolysis, and then all leucocytes are trapped by antibody immobilized-magnetic beads. The antibody used in antibody magnetic beads for the negative selection is selected from a group of antibodies against surface markers which are expressed on all leucocytes, but not expressed on CTCs, CECs and/or CEPs. For example, the marker may be selected from a group of CD2, CD3, CD4, CD5, CD8, CD10, CD11b, CD14, CD15, CD16, CD19, CD20, CD24, CD25, CD27, CD29, CD33, CD36, CD38, CD41, CD45, CD45RA, CD45RO, CD56, CD66b, CD66e, CD69, and CD124. Cells which are not bound to the magnetic beads immobilized with the above antibody are specifically, fluorescently stained with the following fluorescence-labeled antibody. That is to say, CTCs are stained with APC fluorescence labeled-anti CD326 antibody, and CECs are stained with AlexaFluor660 fluorescence-labeled-anti CD146 antibody. Further, CEPs are stained with AlexaFluor680 fluorescence labeled-anti CD34 antibody. In FIG. 11(a), fluorescence spectra of fluorescent molecules i.e. APC, AlexaFlou660, and AlexaFlou680, which can be excited by red lasers at 640 nm, are shown. As shown in FIG. (b), CTCs, CECs, and CEPs are found on different lines respectively, according to the relationships of fluorescence signal intensities of FL3 and FL4. Therefore, CTCs, CECs, and CEPs can be counted separately. In this case, APC-Cy7 fluorescence labeled-anti CD45 antibody is not necessary, because leucocytes are removed by negative selection. Further, in this method, determinations of life or death of cells explained in FIG. 7(b) can be carried out on CTCs, CECs, and CEPs respectively, by nuclear staining with SYTO9 and PI.

Advantageous Effects of Invention

In the conventional method, it is impossible that living CTCs can be concentrated and stained in a living state, and the living CTCs and dead CTCs are simultaneously and separately measured respectively. The above problems can be solved by the method of the present invention. According to the present invention, concentrations of living CTCs which may metastasize and of dead CTCs which may not metastasize, can be evaluated, and therefore, information for determining therapeutic effects of anticancer drug or radiation therapy, or determining the progress of cancer metastasis, can be obtained. That is, living CTCs detected in each patient can be collected and cultured. An adequate amount of CTCs may be used for a genetic analysis for determining therapeutic strategy, and analysis of surface markers of the CTCs. Further, the CTCs can be contributed to a development of molecular target antibody drugs in the pharmaceutical industry.

According to the method for evaluating the number of specific cells and the method for evaluating a concentration of CTCs, a small amount of cells can be collected with an excellent detection efficiency. That is, a small amount of cells are added to a large amount of cells, and a detection efficiency of the small amount of cells is measured according to the method of the present invention. As a result, the detection efficiency of the small amount of cells was about 100%. This is because, in the present invention, it is possible that the whole sample liquid can flow directly into the micro flow path from the bottom of the sample reservoir, and the end point of the whole sample liquid can be detected by air bubbles generated after finishing a flow of the whole sample liquid

BRIEF DESCRIPTION OF THE DRAWINGS

FIG. 6 is a view showing the APC spectra in two types of fluorescence signals at different wavelengths, and a method for identifying the same.

FIG. 8(a) is graphs showing a procedure of automatic live CTC identification. FIG. 8(b) is graphs showing a procedure of automatic dead CTC identification. FIG. 8(c) is a graph showing an effect of removal of non-specific APC stained cells.

DESCRIPTION OF EMBODIMENTS

Figure 1A:
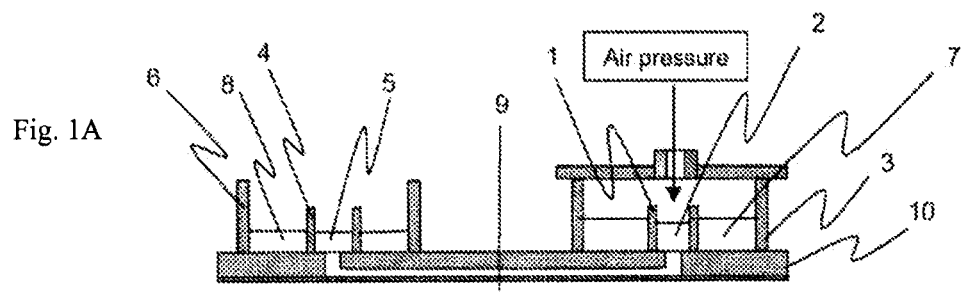
FIG. 1 is a view showing the disposable microfluidic chip for the flow cytometer of the present invention wherein a cross-contamination between samples is not observed. The cross-sectional view (a), top side view (b), and micro flow path pattern (c) are shown respectively.

In a method for detecting and counting the CTCs, low numbers of specific cancer cells (about 1 cell/mL) are detected from and counted in various cell populations containing erythrocytes and leucocytes (about $10^9$ cells/mL). In the following examples, a method wherein about 2 to 9 CTCs may be detected in 4 mL of peripheral blood, and the resulting data, are explained
1 Pretreatment Step of CTC
1-1 Step for Blood Collection In order to count CTC alive, a blood collection tube which causes damage to cells, cannot be used. As the blood collection tube for detecting CTCs, a CellSave Preservative Tubes is used in CellSearch System. However, the collection tube causes damage to cells. Therefore, it is impossible for the collection tube to be used in the method wherein cells are measured alive, and then collected and cultured. In other words, in the method for measuring CTC according to the CellSave system, it is impossible to measure the CTCs alive. In order to solve the above problem, it is preferable to use, for example, a blood collection tube containing EDTA in which the CTCs can be stored alive.
1-2 Hemolysis Step The pretreatment step, in which the peripheral blood collected from a patient is treated, may comprise a hemolysis step for removing erythrocytes. There is a method for separating leucocyte's layer from erythrocyte's layer by a density-gradient centrifugation. However, CTCs have various densities, and therefore, it is not ensured that the densities of all CTCs are lower than that of erythrocytes. Thus, it is preferable to remove the erythrocytes from the various cell populations by the hemolysis method which is a more stable method. A volume of blood sampling is in the constant range i.e. 4 mL to 7 mL.
1-3 Antibody Reaction Step The treatment for concentrating CTCs derived from epithelial cells alive, and the treatment for specifically fluorescence-staining CTCs derived from epithelial cells alive, will be described hereinafter. For the above two treatments, any one of the following three types of combinations of antibody immobilized-magnetic beads and fluorescence labeled antibodies, i.e. Type A, Type B, and Type C, may be used. In the case of Type A, anti CD326 antibody immobilized-magnetic beads (Miltenyi Biotec, Catalog #130-090-500) can be used. In connection to this, it is preferable that a magnet manufactured by Miltenyi Biotec is used, when the above magnetic beads are used. Further, APC labeled anti-CD326 antibody is used. APC-Cy7 fluorescence labeled anti-CD45 antibody can specifically bind to leucocytes, to thereby distinguish leucocytes to which APC fluorescence is non-specifically bound to CTCs. It can be understood that the staining leucocytes with APC-Cy7 fluorescence labeled anti-CD45 antibody is necessary, from the graph of FIG. 8(c). That is, many leucocytes are included in the concentrated cells by the magnetic beads. The EpCAM should be expressed on CTCs derived from epithelial cells in blood only. However, APC labeled anti-CD326 antibody may non-specifically bind to leucocytes. In order to distinguish the non-specific binding of APC to leucocytes from the specific binding of APC to CTCs, the leucocytes are stained with APC-Cy7 fluorescence labeled anti-CD45 antibody which is specifically bound to leucocytes. Through staining, the linear region surrounded by a broken line in FIG. 8(c) which is shifted from the line of the APC spectrum, is found. An accurate number of CTCs can be counted by removing the cells in the linear region.

In the case of Type B, magnetic beads manufactured by Stem Cell Technologies (Catalog #18356) can be used. Further, it is preferable that a magnet manufactured by Stem Cell Technologies is used. As the fluorescence-labeled antibody, the APC labeled 5E11 antibody, which is prepared separately, is used.

Figure 1B:
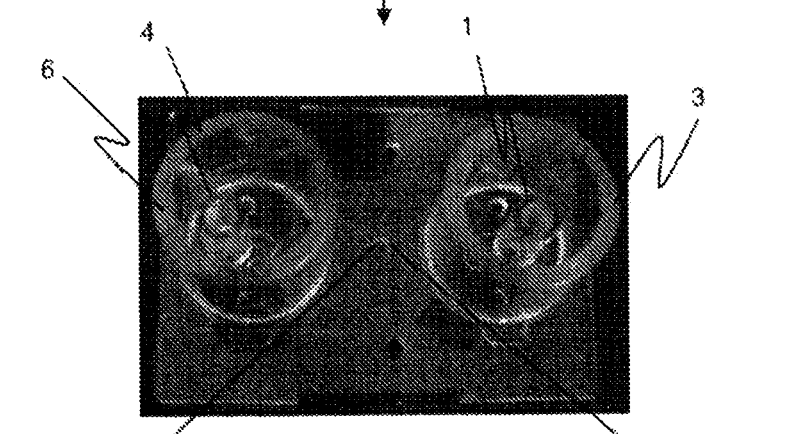
Figure 1C:
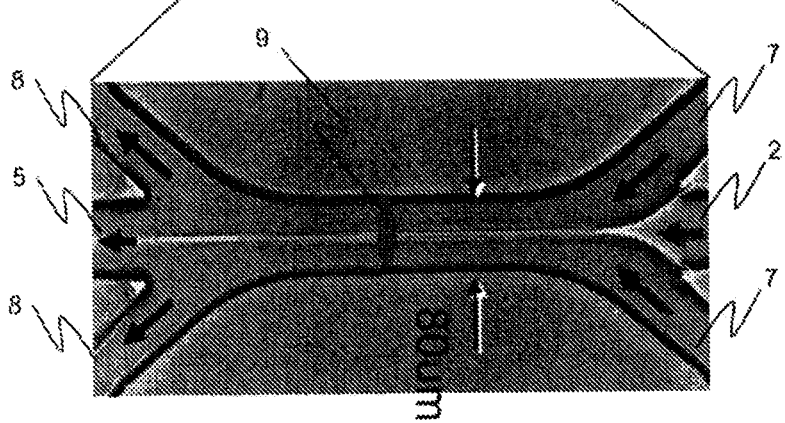
Figure 2:
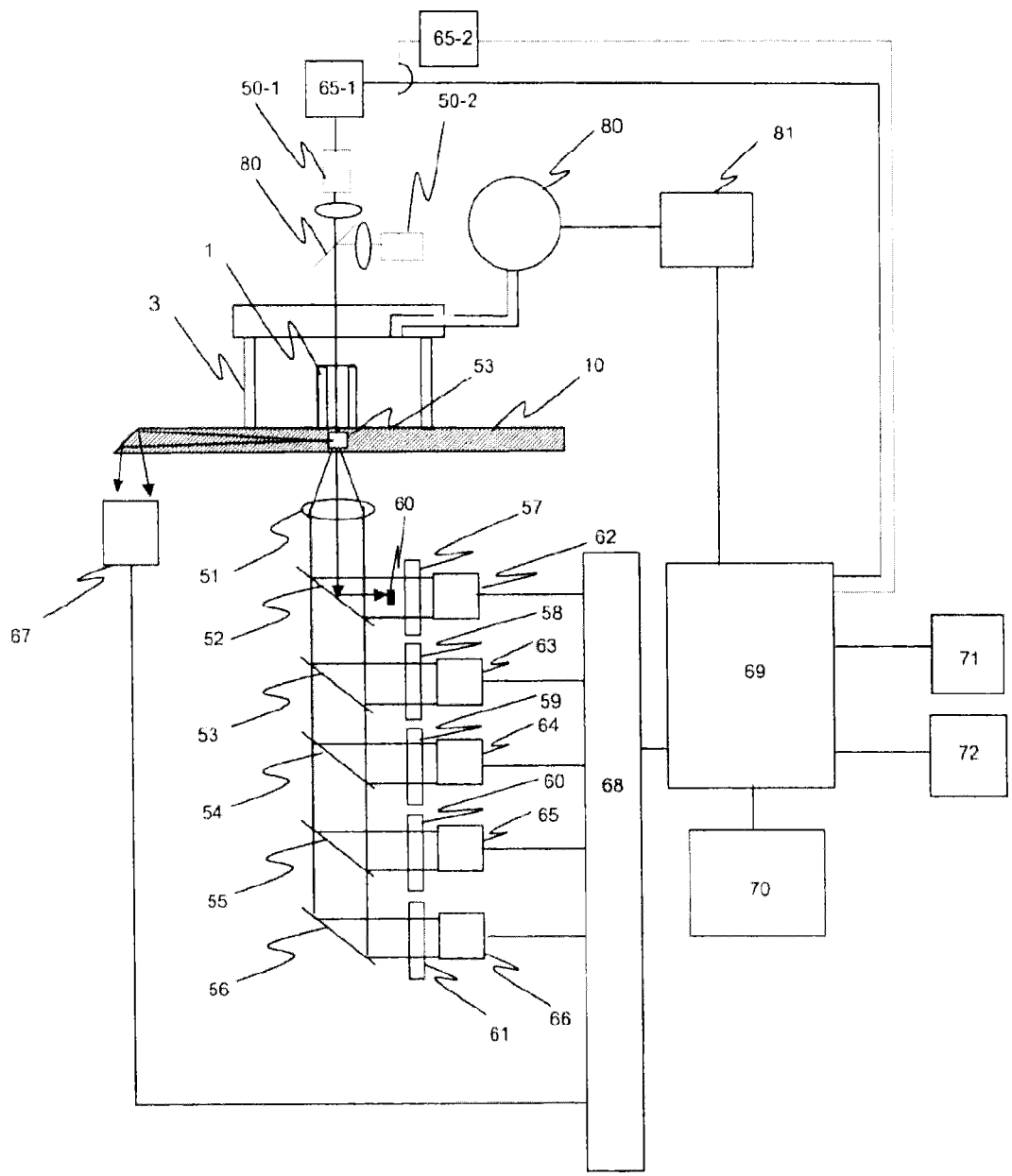
FIG. 2 is a view showing the entire constitution of a detection system containing an optical system for irradiation and an optical system for detection of the flow cytometer of the present invention, wherein a cross-contamination between samples is not observed and the total volume of the sample can be measured.
Figure 3A:
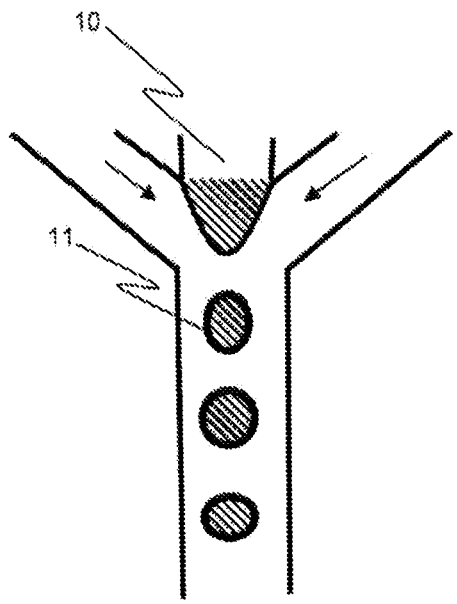
FIG. 3 is a view of developed air bubbles used as an end point signal of a sample liquid (a), a scatter diagram of data with air bubble signals (b), and a scatter diagram of data without air bubble signals (c) in the case that the total volume of the sample is measured using the disposable micro flow-path chip in the present invention.
Figure 3B:
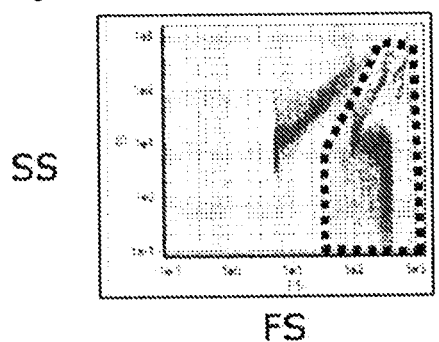
Figure 3C:
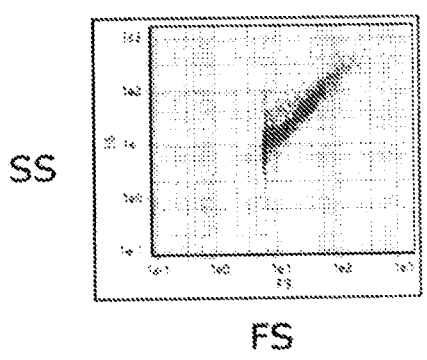
Figure 4:
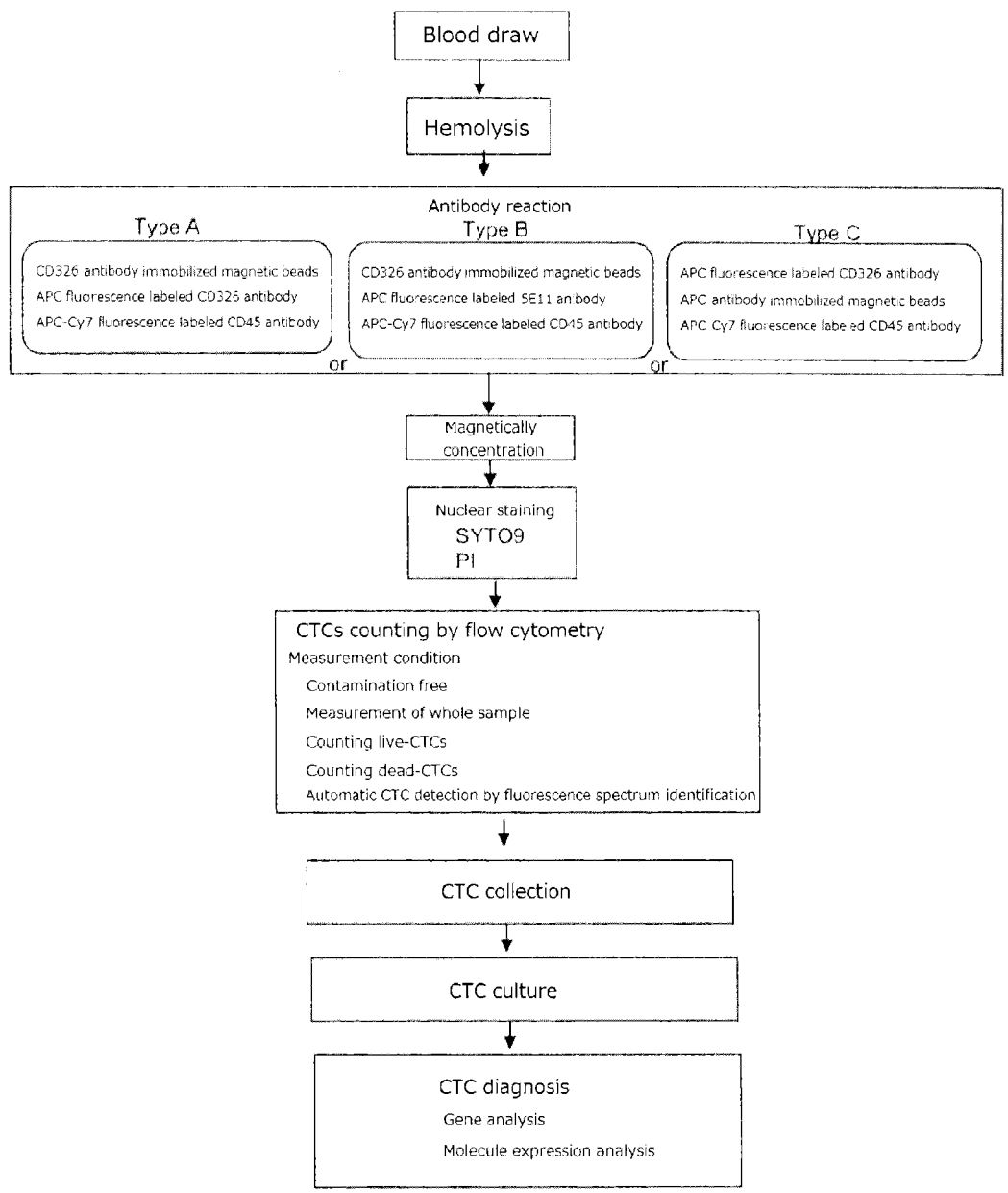
FIG. 4 is a flow chart of a process for sample treatment in the present invention.
Figure 5A:
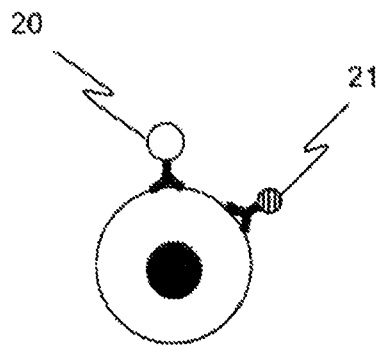
FIG. 5 is a view showing the antibody immobilized-magnetic beads and the fluorescence labeled antibody binding to a CTC in Type A (a), Type B (b), and Type C (c) in FIG. 4.
Figure 5B:
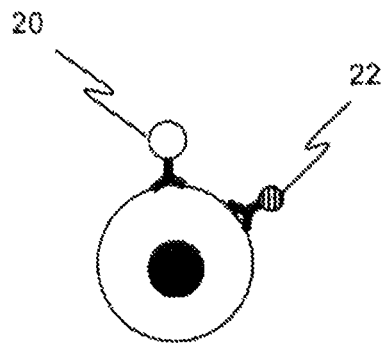
Figure 5C:
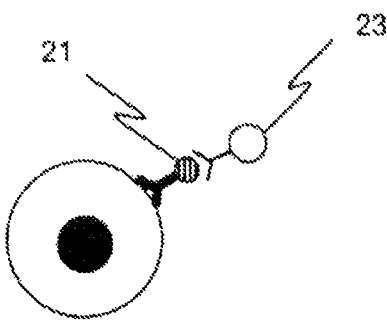
Figure 6A:
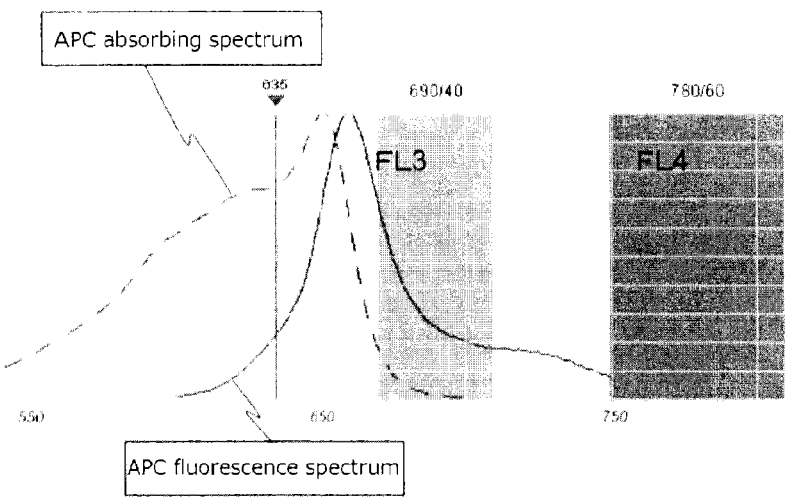
FIG. 6(a) shows the APC fluorescence spectrum and two types of detected fluorescence wavelength regions.
Figure 6B:
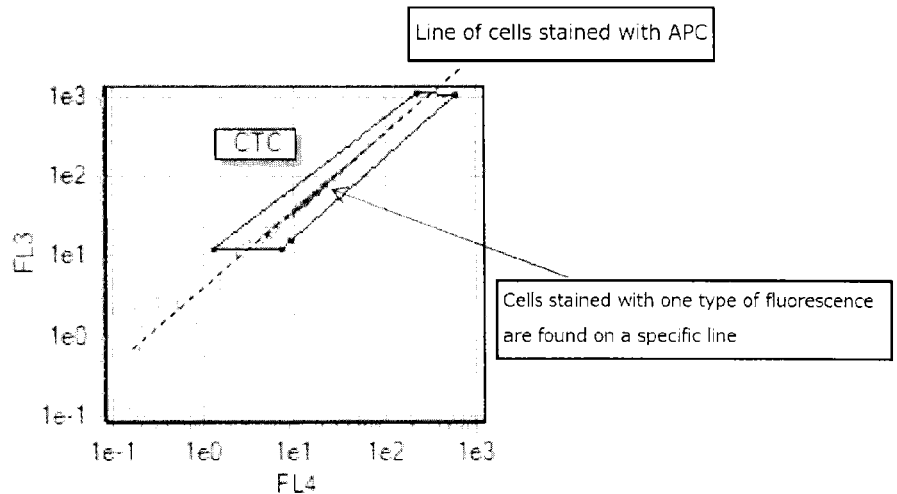
FIG. 6(b) shows a principle for identifying the APC fluorescence spectrum on the basis of the rate of the two types of fluorescence detection signals.
Figure 7A:
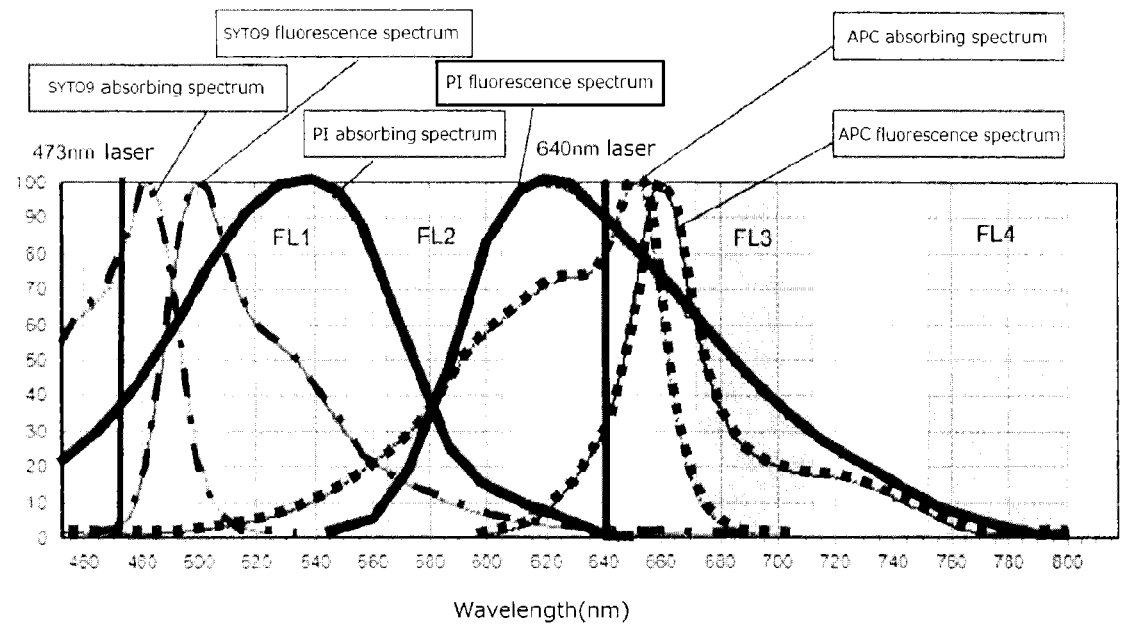
FIG. 7 is a graph of fluorescence spectra (a) showing a problem in identification of the APC fluorescence spectrum of the CTC and the determination of life or death of CTCs, and graphs (b) showing the effects of solving the problems. In the graph (b), the determination of life or death of CTCs carried out after identifying CTCs by the APC fluorescence spectrum.
Figure 7B:
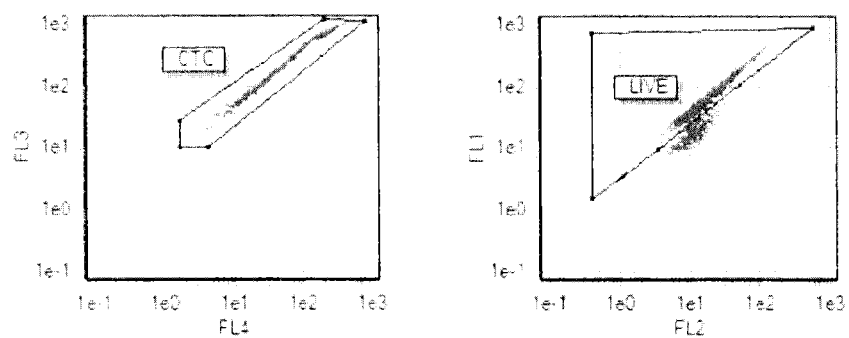

In the case of Type C, the APC fluorescence-labeled anti CD326 antibody is used as the fluorescence-labeled antibody, and magnetic beads, which may bind to the APC, are used. As the magnetic beads, APC antibody immobilized magnetic beads Stem Cell Technologies, Catalog #18451) can be used. Further, it is preferable that a magnet manufactured by Stem Cell Technologies is used. In addition, leucocytes which are non-specifically stained with APC fluorescence are distinguished from CTCs by staining the leucocytes with APC-Cy7 fluorescence labeled anti CD45 antibody.
1-4 Magnetic Concentration Step In the magnetic concentration step, cells other than CTCs are washed out by a buffer while trapping CTCs bound to magnetic beads by a magnet. The magnet is appropriately selected according to the type of magnetic beads used in this step, because needed magnetic forces are varied according to the type of magnetic beads, as mentioned above. Further, the magnetic beads may sometimes bind to cells other than CTCs, and thus the purity of CTCs is not very high, even after the magnetic concentration step. Therefore, it is important to stain the cells other than CTCs with APC-Cy7 fluorescence labeled anti CD45 antibody.
1-5 Nuclear Staining to Determine Whether a CTC is Alive or Dead In this step, BacLight kit (Invitrogen, Catalog No. L34856) is used. The reagent kit contains two types of nuclear staining reagents i.e. one being permeable cell membrane SYTO9 and the other being non-permeable cell membrane PI. The reagent kit is for determining whether bacterium is alive or dead, but can be used for cells by being diluted by a factor of about 100. The right scatter diagram of FIG. 7(b) is a graph showing that life or death of PC-9 cells is determined by using the reagent kit. A cell stained with only SYTO9 is determined as a living cell, and a cell stained with both SYTO9 and PI is determined as a dead cell. That is, the life or the death of cell is determined by the difference of fluorescence spectrum of the cell.
2 Step for Counting CTCs
2-1 Step for Measuring the Total Volume of a Sample of CTCs In order to count an infinitesimal amount of CTCs contained in a clinical sample at short times, and further collecting the CTCs and culturing the obtained CTCs, it is most appropriate that the flow cytometer wherein a cross-contamination between samples is not observed, is used. As such flow cytometer, the FISHMAN-R manufactured by On-Chip Biotechnologies can only be used. This flow cytometer is disclosed in PATENT LITERATURE 4. As shown in FIG. 1, the entire liquid-feeding system is replaceable by using the disposable chip as a flow cell. Therefore, in the flow cytometer, the cross-contamination between samples is not completely observed. The measurement of the total volume of a sample which can be conducted by the flow cytometer, will be explained hereinafter according to FIGS. 1, 2, and 3. FIG. 1 shows a conformation of the disposable chip, and particularly, the cross-sectional view thereof (a), a photograph (b), and a photograph of micro flow path pattern (c) are shown. A sample liquid 2 containing CTCs is poured into sample reservoir 1 after removing an upper cover of sheath liquid reservoir 3 arranged on the right side of the chip. A maximum volume of the sample reservoir is 200 μL. A maximum volume of the sheath liquid reservoir is 300 μL. A sheath liquid 7 is poured into the sheath liquid reservoir 3. In the liquid-feeding system, the sample liquid flows downstream by applying air pressure to the inside of reservoir 3, without bringing a device of the flow cytometer into contact with the sample liquid. Regarding a volume of sheath liquid, sheath liquid remains at the sheath liquid reservoir just as the total volume of sample liquid flows out. As shown in FIG. 1), the sample liquid is connected to the micro flow paths on the downstream. The sample liquid 2 is narrowed by the sheath liquid 7, and flows. A laser light 9 is illuminated onto the site where the sample flows. At the downstream side, the sample liquid is separated from the sheath liquids, and a collected liquid 5 containing CTCs are recovered from the collection reservoir 4. FIG. 2 shows the total measurement system. As illuminated lasers, two types of lasers i.e. a blue laser with emission wavelength ranging from 470 to 490 nm, and a red laser with emission wavelength ranging from 630 to 650 nm, are used. A scattered light detecting system comprises a forward-scattered light detector 62, and a side-scattered light detector 67. Further, in the optical system for detecting fluorescence, an apparatus having a detector which can detect 4 or more fluorescence is used. Four fluorescence at four detecting regions i.e. FL1, FL2, FL3, and FL4 shown in FIG. 7, are detected by detectors 63, 64, 65, and 66, respectively. The respective range of detected wavelength is defined by the reflectance property of a dichroic mirror 55, 56, or 57, and transmission characteristics of a band-pass filter 58, 59, 60, or 61. FIG. 7(A) shows wavelength regions of FL1, FL 2, FL 3, and FL 4. The side-scattered light detector 67 detects a side-scattered light which is developed in the micro flow path and is totallyreflected by an inclined surface at an end face of a chip. The detection signal of a single cell is digitalized by an AD converter 68 and an arithmetic processing of the detection signal is performed by a control computer 69. The flow rate is controlled by applying a predetermined pressure to the reservoir of a chip by an air pump 80. FIG. 3(a) is a view showing that the air bubbles are developed at a junction of flow paths when the sample liquid 2 flows out from the sample reservoir 1. FIG. 3(b) shows the distribution of detection data including the data of the air bubbles developed after all of the sample liquid flows out. The air bubbles develop just after the sample liquid is finished. Thus, a scatter diagram of data of cells only which does not include data of air bubbles may be obtained, by removing data in order from last data in detection time (FIG. 3(c)). Therefore, when predetermined numbers of air bubbles are counted in a region wherein the air bubbles are founded, the flow cytometry is automatically stopped. Further, the data of air bubbles is removed from the detection data, in order from the last data.

2-2 Step for Automatically Recognizing Living CTCs and Dead CTCs

FIG. 8(a) shows that a certain level or more threshold of FS signal is determined in the data wherein the data of air bubbles is removed after the total volume of the sample is measured. The threshold level is determined so as to remove free fluorescence labeled antibodies which are not bound to cells.

Next, a distribution of cells stained with APC is selected in the graph showing a relationship between FL3 fluorescence intensity and FL4 fluorescence intensity. The selected distribution region includes CTCs.

Further, cells nuclear-stained only with SYTO9 and cells nuclear-stained both with SYTO9 and PI are recognized in the graph showing a relationship between FL3 fluorescence intensity and FL4 fluorescence intensity, and thereby, living cells and dead cells can be recognized separately. The number of living CTCs is counted by selecting a distribution region of living cells. FIG. 8(b) shows a procedure for counting dead CTCs, and the number of dead cells is counted by selecting a distribution region of dead cells in the graph showing a relationship between FL1 and FL2.

Figure 9:
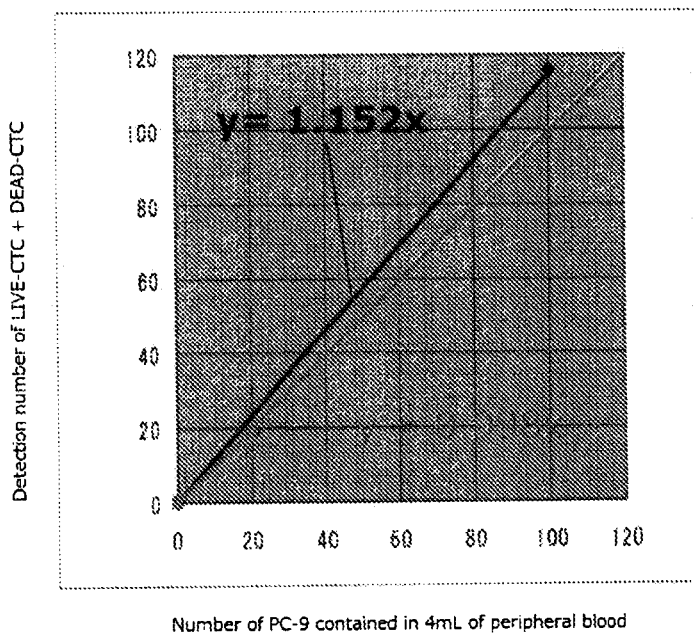
FIG. 9 is a graph showing an analysis data of detecting PC-9 cells from a sample in which PC-9 cells which are cell lines derived from lung cancer patient, are added to a peripheral blood.

FIG. 9 is a graph showing that PC-9 cells which is cell line derived from lung cancer patient, are added to 4 mL of peripheral blood, and the PC9 cells are counted by the above steps using an antibody reagent kit of Type A, to obtain the detection efficiency of PC9 cells. An abscissa axis is the number of added PC-9 cells counted using a counting chamber, and a longitudinal axis is the total number of living CTCs and dead CTCs counted using FISHMAN-R. FIG. 9 shows two results of different experiments. In each experiment, about 100% of detection efficiency is obtained.

3 Step for Collecting CTCs and Culturing CTCs.

This step will be explained according to FIG. 10. In the micro flow path pattern of the chip used for collecting, three flow paths which are branched off downstream, and three flow paths which are joined upstream, are symmetrically arranged. Therefore, the sample liquid and the sheath liquid flowing on both sides of the sample liquid are separated again on the downstream side, to thereby collect the sample liquid into the center reservoir.

Figure 10:
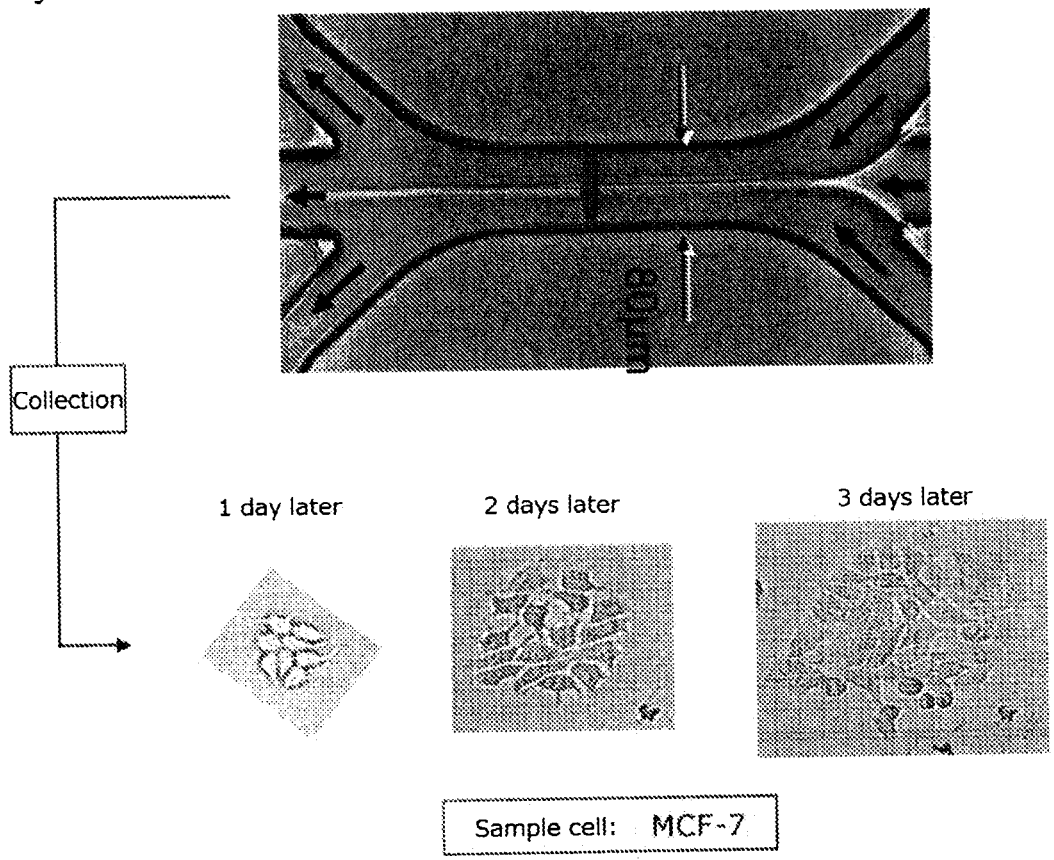
FIG. 10 is a set of photographs showing that fluorescently-stained cells are measured by using a disposable micro flow path chip, and then the cells are collected and cultured, to thereby proliferate.

The photographs of FIG. 10 show the cultured MCF-7 cells which are added to peripheral blood, detected therein, and recovered therefrom.

4 Diagnoses of CTCs

CTCs in a patient are counted, and then collected. Further, if necessary, the collected CTCs are cultured, and genetically analyzed by the FISH method or PCR method. For example, molecular target drugs for effectively treating a patient can be selected by detecting an enhancement of the HER2 gene, a mutation of the EGFR gene, or the like.

In the method of the present invention, life or death of CTCs is determined, and the CTCs are counted alive. Further, the CTCs are collected alive, so as to obtain CTCs which can be cultured. Then, the diagnosis of CTCs can be carried out.

Next, the embodiment for accurately evaluating a cancer progression by simultaneously detecting other biomarker(s) such as CEC and/or CEP in addition to CTC, will be explained hereinafter. In the treatment for concentrating CEC and/or CEP which are detected along with CTC, the negative selection is used. The negative selection includes a method wherein the magnetic beads are not used (for example, Tumor Cell Enrichment Cocktail (Stem Cell Technologies, Catalog #15167)), and a method wherein the magnetic beads are used.

In the method using the magnetic beads, erythrocytes are removed by hemolysis, and then all leucocytes are trapped by antibody immobilized-magnetic beads. The antibody used in antibody magnetic beads for the negative selection is selected from a group of antibodies against surface markers which are expressed on all leucocytes, but not expressed on CTCs, CECs and/or CEP. For example, the marker may be selected from a group of CD2, CD3, CD4, CD5, CD8, CD10, CD11b, CD14, CD15, CD16, CD19, CD20, CD24, CD25, CD27, CD29, CD33, CD36, CD38, CD41, CD45, CD45RA, CD45RO, CD56, CD66b, CD66e, CD69, and CD124. In both methods wherein the magnetic beads are used and not used, the cells obtained by the negative selection are specifically stained with fluorescence labeled antibodies as follows. That is to say, CTCs are stained with APC fluorescence-labeled anti CD326 antibody, CECs are stained with AlexaFluor660 fluorescence-labeled anti CD146 antibody, and CEPs are stained with AlexaFluor680 fluorescence-labeled anti CD34 antibody.

Figure 11A:
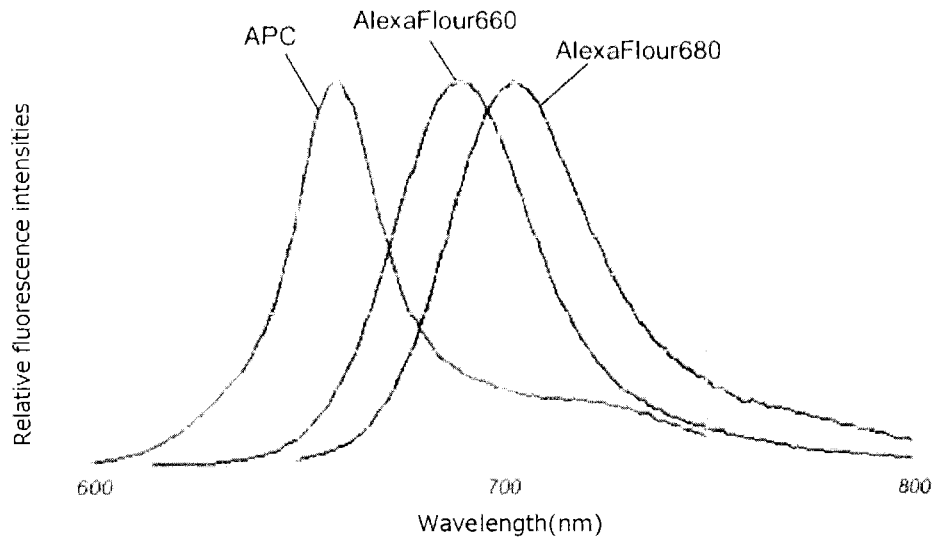
FIG. 11(a) is a graph showing fluorescence spectra of a fluorescent molecules used in the detection of CEC or CEP in addition to CTC from peripheral blood.
Figure 11B:
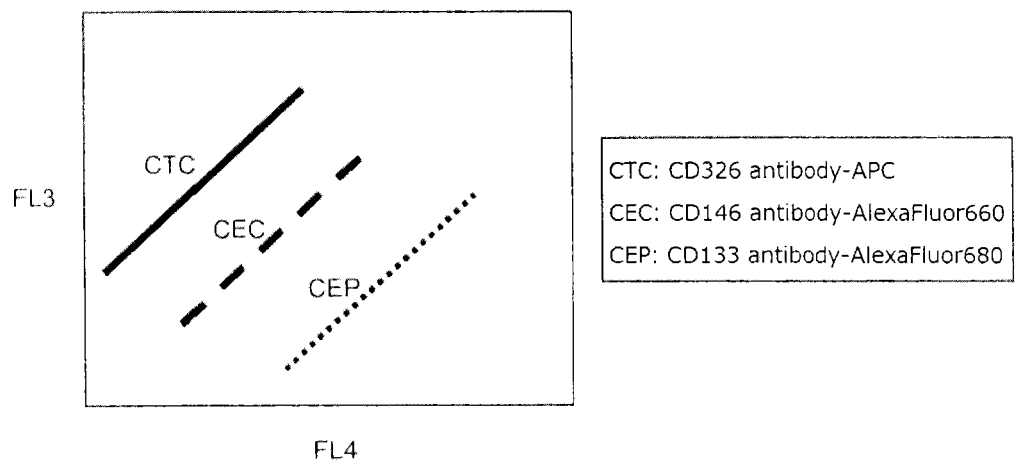
FIG. 11(b) is a graph showing a principle for separating three types of fluorescence by each rate of the two fluorescence signal intensities.

FIG. 11(a) is a graph showing fluorescence spectra of APC, AlexaFlou660, and AlexaFlou680 which are fluorescence molecules for labeling. All fluorescence molecules can be excited by red lasers of 640 nm. Cells stained with APC, cells stained with AlexaFlou660, and cells stained with AlexaFlou680 are distributed on different lines respectively by the relationships between FL3 fluorescence signal intensity and FL4 fluorescence signal intensity, shown in FIG. 11(b). Thus, CTCs, CECs, and CEPs can be separately counted. In this case, it is not necessary to stain with APC-Cy7 fluorescence labeled anti CD45antibody, because the leucocytes are removed by the negative selection. In this method, life or death of CTCs, CECs, or CEPs is determined by nuclear staining thereof, as shown in FIG. 7(b).

INDUSTRIAL APPLICABILITY

The present invention has the following advantageous effects. (1) A patient can be diagnosed with cancer by detecting CTCs only using blood collected from the patient. (2) A cancer recurrence in a patient wherein cancer tissue is extirpated by surgery can be detected early. (3) CTCs of each patient are detected and collected, and then the gene analysis thereof, the expression analysis of the surface marker thereof, and drug screening thereto, can be carried out. Therefore, an effective molecular target drug can be decided, and thus the present invention can contribute a personalized therapy in hospital or a development of a molecular target drug in pharmaceutical companies.

Although the present invention has been described with reference to specific embodiments, various changes and modifications obvious to those skilled in the art are possible without departing from the scope of the appended claims.

REFERENCE SIGNS LIST

1 . . . Sample reservoir
2 . . . Sample
3 . . . Sheath liquid reservoir
4 . . . Collection reservoir
5 . . . Collected sample
6 . . . Waste sheath liquid reservoir
7 . . . Sheath liquid
8 . . . Waste sheath liquid
9 . . . Illuminated laser light
10 . . . Air
11 . . . Air bubbles
12 . . . Chip substrate
20 . . . anti CD326 antibody immobilized-magnetic beads
21 . . . APC fluorescence labeled anti CD326 antibody
22 . . . APC fluorescence labeled 5E11 antibody
23 . . . Anti APC antibody immobilized-magnetic beads
50-1 . . . Laser light source at wavelength of 473 nm
50-2 . . . Laser light source at wavelength of 640 nm
51 . . . Object lens
52, 53, 54, 55, 56 . . . Dichroic mirror
57, 58, 59, 60, 61 . . . Band-pass filter
60 . . . Spatial filter for blocking a transmission laser light
62 . . . Photodiode
63, 64, 65, 66 . . . Photomultiplier
65-1 . . . Driver circuitry for laser light source at wavelength of 473 nm
65-2 . . . Driver circuitry for laser light source at wavelength of 640 nm
68 . . . AD converter
69 . . . AD converter
70 . . . keyboard
71 . . . Display
72 . . . Mouse
80 . . . Air pump
81 . . . Driver circuitry for air pump

The invention claimed is:

1. A method for enumeration of specific cells present in highly dense cells, characterized by comprising:
the pretreatment step of concentrating the specific cells, and fluorescence staining said cells, and
the step of counting all the specific cells in the sample liquid by automatically identifying said cells based on fluorescence signal intensity thereof;
wherein, in the counting step, the specific cells are counted by measuring a whole sample liquid by a flow cytometer having a disposable micro flow-path chip as a flow cell, the micro flow-path chip containing a sample reservoir, a collection reservoir, and a micro flow-path connected from the bottom of the sample reservoir to the bottom of the collection reservoir on a substrate; and an end point of the whole sample liquid is recognized by a detection of air bubbles generated in the micro flow-path just when the sample liquid in the sample reservoir flows out.

2. The method for enumeration of the specific cells according to claim 1, wherein the specific cells are concentrated alive in the pretreatment step and the numbers of living cells and dead cells of the specific cells are separately counted in the counting step.

3. A method for enumeration of circulating tumor cells (CTCs) by detecting the CTCs present in peripheral blood containing highly-dense blood cells, characterized by comprising:
the pretreatment step including a treatment for concentrating the CTCs and a treatment for fluorescence staining the CTCs, and
the step of identifying and counting the CTCs;
wherein, the pretreatment step comprises a treatment for concentrating CTCs by binding magnetic beads to EpCAM, which is expressed on CTCs derived from epithelial cells using a magnet, and a treatment for fluorescence staining the CTCs with anti-EpCAM antibody; and
in the CTC identifying and counting step, CTCs are counted by measuring a whole sample liquid using a flow cytometer having a disposable micro flow-path chip as a flow cell, which contains a sample reservoir, a collection reservoir, and a micro flow-path connected from the bottom of the sample reservoir to the bottom of the collection reservoir on a substrate, and an end point of the whole sample liquid is recognized by a detection of air bubbles generated in the micro flow-path just when the sample liquid in the sample reservoir flows out.

4. The method for enumeration of circulating tumor cells (CTCs) according to claim 3, wherein the pretreatment step further comprises treatments of two types of nuclear staining, one being cell membrane permeable nuclear staining and the other being cell membrane non-permeable nuclear staining; and in the identifying and counting step, the number of the CTCs are measured separately, divided into living CTCs and dead CTCs.

5. The method for enumeration of circulating tumor cells (CTCs) according to claim 4, wherein the pretreatment step comprises a treatment for concentrating CTCs by binding anti-EpCAM antibody-immobilized magnetic beads to CTCs using a magnet, a treatment for fluorescence staining the CTCs with an APC labeled anti-EpCAM antibody, and a treatment for nuclear staining of the CTCs with SYTO9 and PI; and in the identifying and counting step, the CTC is recognized by identifying the APC fluorescence spectrum using a ratio between two types of fluorescence signal intensities generated by light excitation at a wavelength of around 640 nm, and life or death of CTCs is determined by the fluorescence signals of SYTO9 and PI, which are generated by light excitation at a wavelength of around 480 nm, in the identifying and counting step.

6. The method for enumeration of circulating tumor cells (CTCs) according to claim 3, wherein the treatment for concentrating CTCs comprises fluorescence staining by the APC labeled anti-EpCAM antibody, and binding anti-EpCAM antibody-immobilized magnetic beads to CTCs.

7. The method for enumeration of circulating tumor cells (CTCs) according to claim 5, wherein a blue laser power for PI fluorescence excitation is one-tenth ($\frac{1}{10}$) or less of a red laser power for APC fluorescence excitation in order to analyze the recognition of CTC by an APC fluorescence signal and the recognition of dead cells by PI simultaneously.

* * * * *